(12) United States Patent
Dunlap et al.

(10) Patent No.: US 7,862,622 B2
(45) Date of Patent: Jan. 4, 2011

(54) PROSTHETIC FOOT WITH ADJUSTABLE HEEL HEIGHT

(75) Inventors: David Dunlap, Portage, MI (US); Aaron Taszreak, China, MI (US); Lars R. Chrisman, Lawton, MI (US); Michael G. Leydet, St. Clair Shores, MI (US); Christopher L. Johnson, Mountain Park, OK (US)

(73) Assignee: College Park Industries, Inc., Fraser, MI (US)

( * ) Notice: Subject to any disclaimer, the term of this patent is extended or adjusted under 35 U.S.C. 154(b) by 587 days.

(21) Appl. No.: 11/759,632

(22) Filed: Jun. 7, 2007

(65) Prior Publication Data

US 2007/0299544 A1    Dec. 27, 2007

Related U.S. Application Data

(60) Provisional application No. 60/811,974, filed on Jun. 8, 2006.

(51) Int. Cl.
  *A61F 2/68*  (2006.01)
  *A61F 2/66*  (2006.01)
  *G05G 1/04*  (2006.01)
(52) U.S. Cl. .............................. 623/53; 623/47; 74/534
(58) Field of Classification Search ............. 623/47–56; 403/37–39; 74/557 M, 578, 527, 529, 533–534
  See application file for complete search history.

(56) References Cited

U.S. PATENT DOCUMENTS

| | | | |
|---|---|---|---|
| 652,001 A * | 6/1900 | Keil ............................. | 74/534 |
| 2,749,557 A * | 6/1956 | Riddle .......................... | 623/50 |
| 4,306,320 A | 12/1981 | Delp | |
| 4,413,360 A | 11/1983 | Lamb et al. | |
| 4,446,580 A | 5/1984 | Furuya et al. | |
| 5,376,133 A | 12/1994 | Gramnas | |
| 5,509,938 A | 4/1996 | Phillips | |
| 5,571,210 A | 11/1996 | Lindh | |
| 5,913,901 A | 6/1999 | Lacroix | |
| 5,957,981 A | 9/1999 | Gramnas | |
| 6,436,149 B1 | 8/2002 | Rincoe | |
| 6,443,993 B1 | 9/2002 | Koniuk | |

(Continued)

FOREIGN PATENT DOCUMENTS

WO    WO-9217135    10/1992

*Primary Examiner*—William H Matthews
*Assistant Examiner*—Marcia Hoffman
(74) *Attorney, Agent, or Firm*—Gifford, Krass, Sprinkle, Anderson & Citkowski, P.C.

(57) ABSTRACT

A prosthetic foot having an adjustable height heel includes a frame portion with an ankle link pivotally supported on the frame portion at a first pivot axis. A detent rod is pivotally connected to the ankle at a second pivot axis, and a detent member is pivotally affixed to the frame portion at a third pivot axis. The detent member is selectively operable to receive and releasably retain a length of the detent rod therein so that the length of the detent rod extending between the second and third pivot axes may be selectably adjusted. When the length of the rod is so adjusted, the angular relationship of the frame portion and the ankle link is changed thereby changing the heel height of the foot. The detent mechanism may be activated by various means including fluidic means, mechanical means, electromechanical means, and the like.

11 Claims, 4 Drawing Sheets

U.S. PATENT DOCUMENTS

| | | |
|---|---|---|
| 6,855,170 B2 | 2/2005 | Gramnäs |
| 7,506,562 B2 * | 3/2009 | Franze et al. ................ 74/575 |
| 2004/0044417 A1 | 3/2004 | Gramnas |
| 2005/0085926 A1 | 4/2005 | Christensen |
| 2005/0109563 A1 | 5/2005 | Vitale et al. |
| 2005/0119763 A1 | 6/2005 | Christensen |
| 2006/0041321 A1 | 2/2006 | Christensen |

* cited by examiner

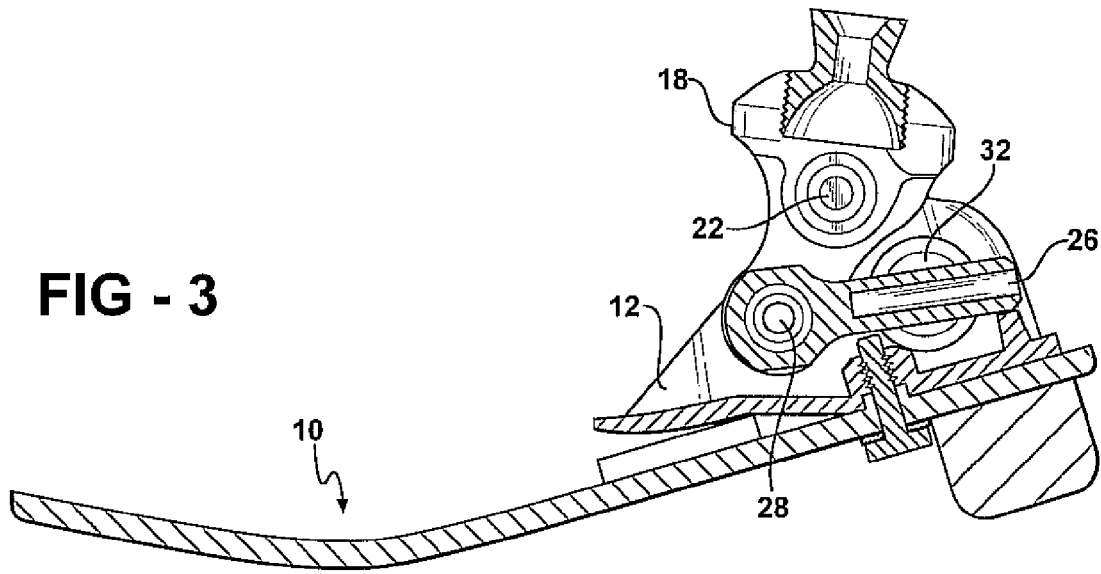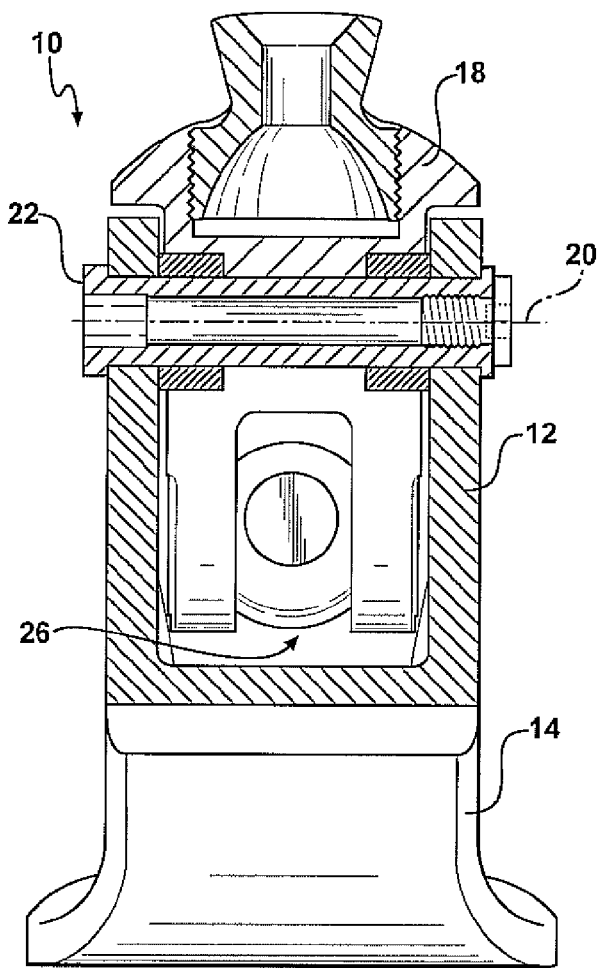

PROSTHETIC FOOT WITH ADJUSTABLE HEEL HEIGHT

CROSS-REFERENCE TO RELATED APPLICATIONS

This application claims priority of U.S. Provisional Patent Application Ser. No. 60/811,974 filed Jun. 8, 2006, entitled "Prosthetic Foot with Adjustable Heel Height."

FIELD OF THE INVENTION

This invention relates generally to prosthetic limbs. More specifically, the invention relates to prosthetic feet. Most specifically, the invention relates to a prosthetic foot wherein the heel height is adjustable.

BACKGROUND OF THE INVENTION

Most prosthetic feet are configured so that the angle formed between the foot and a prosthetic leg joined thereto is fixed. As a consequence, the heel height cannot be varied, and this can present problems when a user switches from one style of shoe to another. The limitations of the fixed angle also prevent a user from dropping or relaxing his or her foot when sitting.

As a consequence, it will be appreciated that there is a need for a prosthetic foot wherein the angle between the foot and the pylon of a prosthetic leg may be user adjustable. Any such adjustment mechanism should be easy and quick to make, and reliable. Also, since prosthetic feet are subjected to high mechanical loadings, any such adjustment mechanism should be sturdy. The prior art has implemented a number of approaches to providing for heel height adjustment in prosthetic feet. These approaches include hydraulic, mechanical and electromechanical devices. In general, prior art adjustment mechanisms have been found to be relatively complicated which can make them expensive and difficult to use.

As will be explained in detail hereinbelow, the present invention provides a heel height adjustment system for prosthetic feet, which system is simple in its construction, reliable, sturdy, easy to use, and capable of providing a fine degree of control over the range of adjustments. In addition, the system of the present invention may be activated by a control which is remote from the foot so as to facilitate adjustments while the foot is in use. These and other advantages of the invention will be explained in detail hereinbelow.

SUMMARY OF THE INVENTION

Disclosed is a prosthetic foot having an adjustable height heel. The foot includes a frame portion and an ankle link which is pivotally supported by the frame portion at a first pivot axis. A detent rod is pivotally connected to the ankle link at a second pivot axis, and a detent member is pivotally affixed to the frame portion at a third pivot axis. The detent member is selectably operable to receive and releasably retain a length of the detent rod so that the length of the detent rod extending between the second and third pivot axes may be selectably adjusted. In this manner, when the length of the detent rod extending between the second and third pivot axes is changed, the angular relationship of the frame portion and the ankle link is changed.

In specific embodiments, the detent rod includes at least one groove formed thereupon, and the detent member includes at least one corresponding groove which may be selectably engaged with the at least one groove of the detent rod. In a specific embodiment, the detent member includes a housing having a slidable member disposed therein. The slidable member has a passage which is configured to allow a segment of an elongated portion of the detent rod to pass therethrough. The detent member further includes a biasing member which is operable to exert a biasing force on the slidable member so as to urge a portion of the wall of the passage into contact with a segment of the detent rod. Biasing may be accomplished by a spring, while in other instances it may be accomplished by an elastic member, a hydraulic or fluidic actuator or the like.

In one specific embodiment, the detent member includes an actuator button which displaces the slidable member against the biasing force so as to free the detent rod. In another embodiment, the detent member has a fluid chamber defined therein which is in fluid communication with the fluid inlet. The fluid chamber is in mechanical communication with a slidable member so that introduction of a fluid into the chamber exerts a force on the slidable member so as to overcome the biasing force. Fluid may be introduced into the chamber by a pump, such as a handheld pump, and in specific instances, the fluid is air. In other instances, activation may be by solenoids, linear actuators, or shape memory material based actuators, other electromechanical or mechanical actuators and the like.

Also disclosed is a detent assembly.

BRIEF DESCRIPTION OF THE DRAWINGS

FIG. 3 is a cross-sectional view of the foot of FIG. 1 taken at a plane approximately through the midline thereof;

FIG. 4 is a cross-sectional view of the foot of FIG. 1 taken transverse to the FIG. 1 view;

DETAILED DESCRIPTION OF THE PREFERRED EMBODIMENTS

The present invention is directed to a prosthetic foot with an adjustable height heel. The adjustability is achieved through the use of a particular mechanical assembly employed in connection with a frame portion of a prosthetic foot. The assembly includes an ankle link which is pivotally supported by the frame portion of the foot at a first pivot axis. This ankle link is configured to attach the foot to a prosthetic leg. A detent rod is pivotally connected to the ankle link at a second pivot axis which is spaced from the first pivot axis. A detent member is pivotally affixed to the frame at a third pivot axis. The detent member engages a portion of the detent rod and is operable to selectably retain that rod. By controlling the detent mechanism, the length of the detent rod extending between the second and third pivot points may be changed, and as this length is changed, the ankle link is pivoted back and forth thereby changing the angular relationship of the ankle link and the remainder of the foot thereby changing the elevation of the heel.

Figure 1:
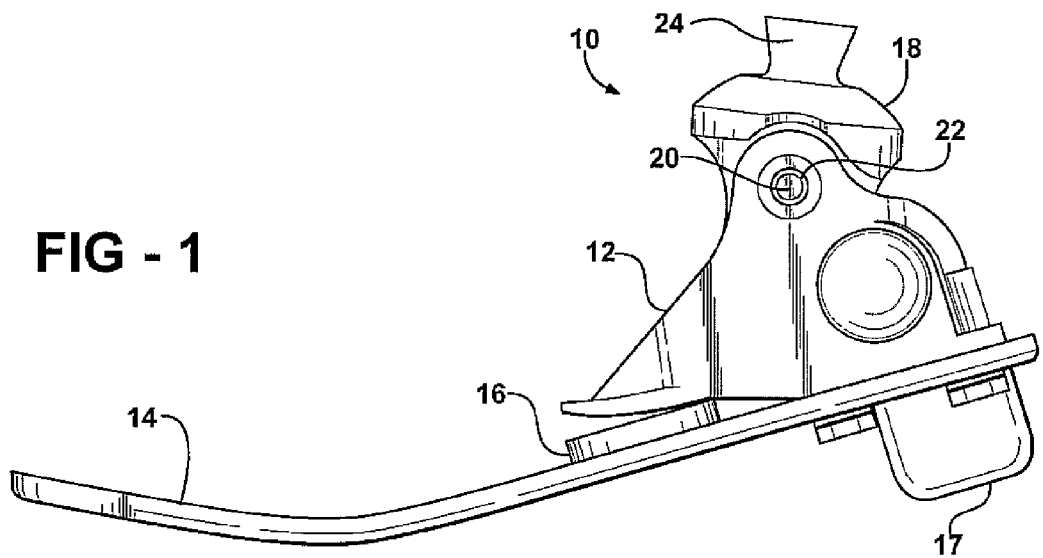
FIG. 1 is a side view of one embodiment of prosthetic foot.

This invention will be explained with reference to one particular embodiment, and it is to be understood that various other embodiments may be implemented in accord with the teaching presented herein. Referring now to FIG. 1, there is shown a side view of one embodiment of prosthetic foot 10 having an adjustable heel feature. The foot 10 includes a frame portion 12 which is typically comprised of a relatively rigid body of strong, lightweight material such as a metal alloy; although, it is to be understood that the frame portion may be fabricated from other materials such as polymeric materials, composites and the like. As shown in the FIG. 1 embodiment, the frame portion further includes a resilient sole plate 14 mechanically affixed thereto. The sole plate 14, in this embodiment, is fabricated from a relatively rigid, fiber reinforced body of polymeric materials. Various configurations of sole plate are known in the prior art and may be readily adapted for use in the various embodiments of the present foot. As is further illustrated in FIG. 1, a compressible body of polymeric material 16 is disposed between the sole plate 14 and the rigid part of the frame portion 12 where it operates to control forward flexing of the foot. Other embodiments may not include this compressible body 16. In this embodiment, a second body of resilient material 17 is disposed to form a heel cushion on the sole plate 14. Again, other embodiments may not include this feature.

The foot 10 of FIG. 1 further includes an ankle link 18 which is pivotally attached to the frame portion 12 through a first pivot axis 20 defined by a pivot pin 22. As further illustrated, the foot link 18 includes a connector 24 configured to attach the foot to the pylon of a prosthetic leg (not shown). Other types of coupling member known in the art, such as socket members, pins, and the like, may be likewise adapted for coupling the foot to a prosthetic leg. In some instances, coupling may be accomplished through the use of a flexible composite member such as a shank or the like.

Figure 2:
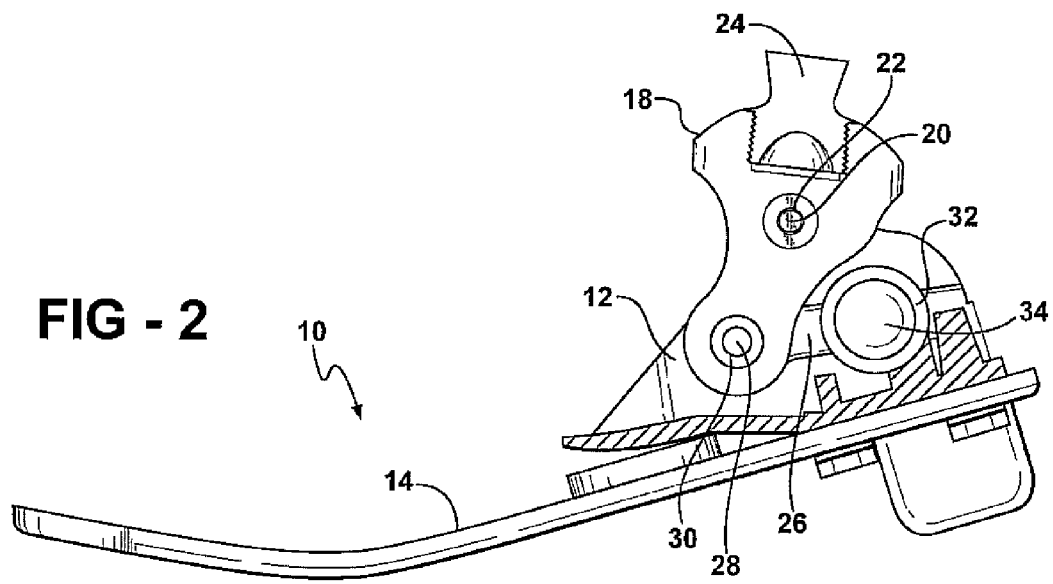
FIG. 2 is a cross-sectional view of the prosthetic foot of FIG. 1.

Referring now to FIG. 2, there is shown a cross-sectional view of the foot 10 of FIG. 1 taken at a first plane longitudinal thereto. In this view, a longitudinal section of the frame 12 is cut away so as to better show details of the ankle link 18, and other portions of the foot 10. As will be seen from FIG. 2, the ankle link 18 is pivotally affixed to the frame 12 via the pivot pin 22 which is aligned with the first pivot axis 20. The pivot pin 22 passes through the ankle link 18 and engages the frame. As will be seen from FIG. 2, the ankle link 18 includes a downwardly projecting lobe portion which is pivotally connected to a detent rod 26 through a second pivot axis 28 which is spaced apart from the first pivot axis 20. The second pivot axis 28 is defined by a lower connector pin 30. This second pivot axis 28, as well as the lower connector pin 30, does not pass through, or otherwise join, to the frame portion 12.

A detent member 32 is pivotally affixed to the frame 12 so as to define a third pivot axis 34. The detent member 32 releasably engages the detent rod 26 and is selectably operable to retain and release the rod so that the length of rod extending between the second 28 and third 34 pivot axes may be adjusted.

Referring now to FIG. 3 there is shown another cross-sectional view of the foot 10 as taken along a plane cut further therethrough in the lengthwise direction. The plane of FIG. 3 lies behind the plane of FIG. 2. Visible in FIG. 3 is the lower portion of the frame 12, a cutaway portion of the ankle link 18 is pivotally affixed to the frame by the top connector pin 22. As will be seen from FIG. 3, the detent rod 26 is pivotally affixed to the downwardly projecting lobe portion of the ankle link 18 by the lower connector pin 28. As will be further seen, a projecting portion of the detent rod 26 engages the detent member 32. As will be explained in detail hereinbelow, the detent member 32 is operable to release and retain the rod 26 so that the length of rod projecting therefrom may be adjusted. It will be appreciated that by varying the length of the rod, the angular relationship of the ankle link 18 and the frame 12 (and hence the sole plate 14) may be varied. By so varying the angular relationship, the heel may be elevated while allowing the prosthetic leg, to be maintained in a fixed angular relationship, typically perpendicular, to the floor.

Referring now to FIG. 4, there is shown a cross-sectional view of the foot 10 taken in a direction transverse to the length of the foot, looking toward the toe end, and generally perpendicular to the view of FIGS. 1-3. As will be seen from FIG. 4, the sole plate 14 is affixed to the frame 12. The ankle link 18 is pivotally affixed to upright portions of the frame 12 by the pivot pin 22, which defines the first pivot axis 20. Also visible in FIG. 4 is an end-on, cross-sectional view of the detent rod 26, and as noted above, this detent rod 26 is pivotally affixed to the ankle link 18 so as to define a second pivot axis. The detent rod 26 is not affixed to the frame 12.

Figure 5:
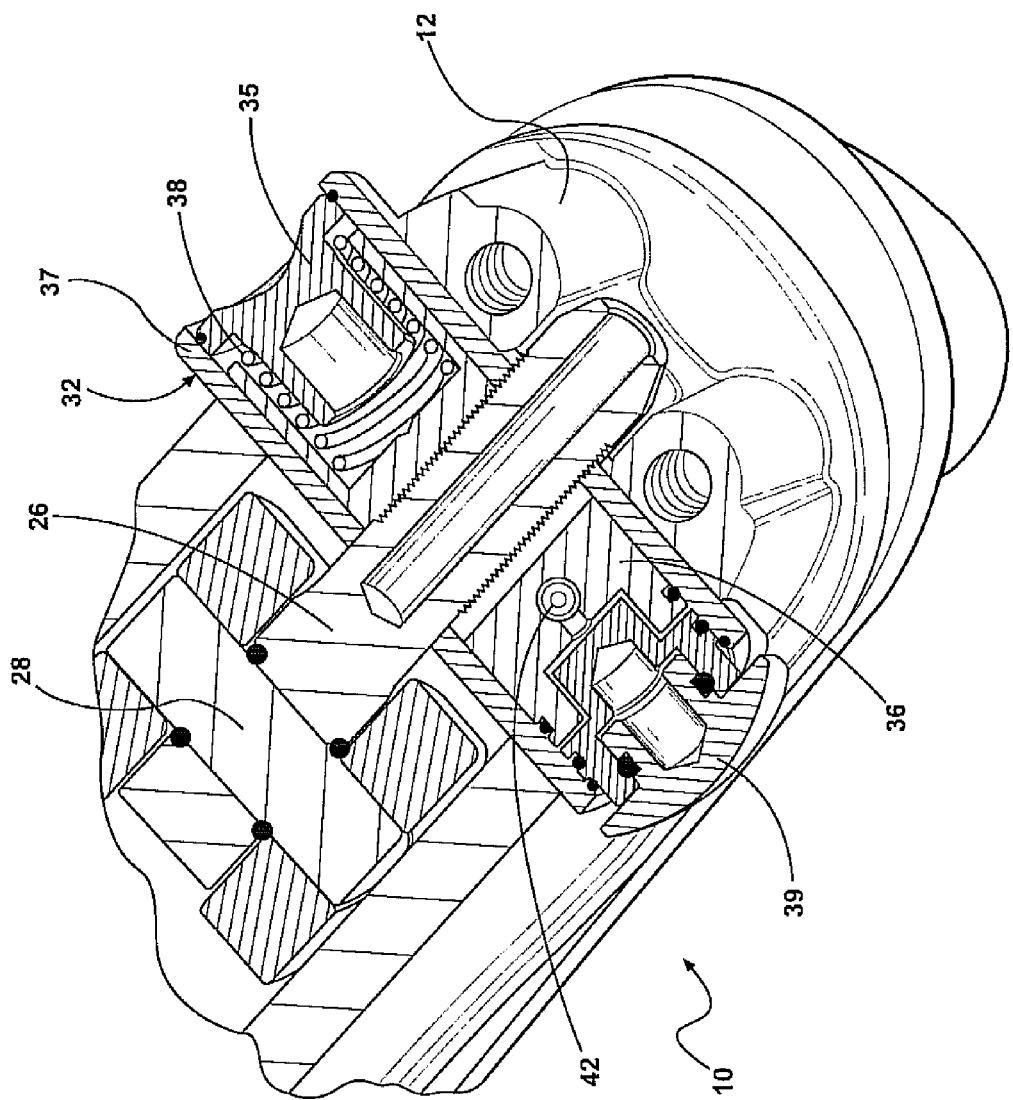
FIG. 5 is a cross-sectional view of a portion of a prosthetic foot taken generally parallel to the sole plate thereof, and illustrating one embodiment of detent mechanism.

Referring now to FIG. 5, there is shown a further cross-sectional view of a portion of the foot 10 taken along a plane roughly parallel to the sole plate 14 of the foot 10. The FIG. 5 view shows details of the detent rod 26 and detent member 32 as disposed and supported within the foot. The detent rod 26 is pivotally supported on the ankle link 18 by the lower pivot 28. The detent member 32 is pivotally supported on the frame 12. As illustrated in FIG. 5, a projecting portion of the detent rod 26 includes a plurality of grooves defined thereupon. In the illustrated embodiment, the grooves are configured as a series of discrete, radial grooves, each encircling the diameter of the elongated portion of the rod; although, it is to be understood that a single helical groove may be used in a similar manner, as may be otherwise configured features, as will be explained hereinbelow. The detent assembly 32 includes a housing 37 having a slidable inner member 36 retained therein. The slidable member 36 has a passageway formed therethrough which is somewhat larger in cross-sectional area than is the cross-sectional area of the portion of the detent rod 26 which passes through the detent assembly 32. The slidable member 36 includes at least one inner surface which is grooved so as to correspond to the grooving in the detent rod 26 and thus serves to engage and retain the detent rod. The detent assembly 32 further includes a spring 38 which is operable to bias the sliding member 36 into contact with the detent rod. It also includes a plunger button 39 which functions as an actuator operable to displace the sliding member 36 against the biasing force of the spring, so as to disengage it from the detent rod 26. It will thus be appreciated that by depressing the button 39, the detent assembly 32 disengages the detent rod 26, thus allowing the portion of the rod passing through the detent assembly 32 to be adjusted, and as noted above, this allows for adjustability of the angular relationship of the frame and ankle link and hence allows for heel height adjustment. The detent member also includes an end cap 35, which functions to retain the spring 38. This end cap may also function as a second actuator button for moving the sliding member into contact with the detent rod 26, in the event of a malfunction or inadequacy of the spring 38.

Figure 6:
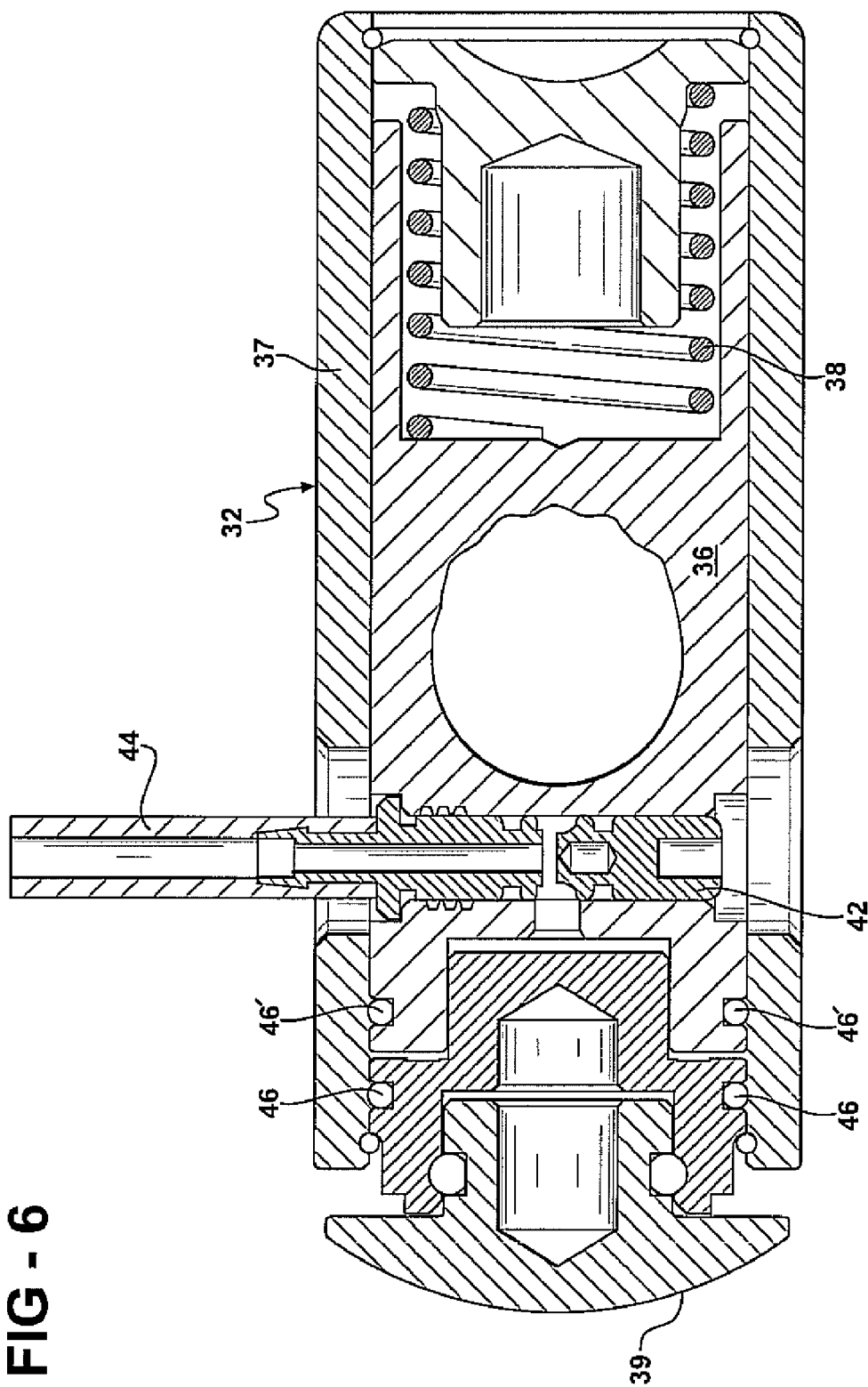
FIG. 6 is a cross-sectional view of one embodiment of fluid activated detent member.

Also visible in this drawing is a fluid inlet port 42, which may be used in conjunction with a fluidic activator which will be described in more detail in FIG. 6.

While in the illustrated embodiment, the detent rod is shown as having a continuous series of discrete radical grooves, it is to be understood that this arrangement may be otherwise implemented. For example, the detent rod may include helical grooving, or otherwise configured features such as projections, recesses, or the like configured so as to be mateable with the detent member as described above. Also, the detent rod and detent member may be configured so as to allow for a series of predetermined angular relationships between the ankle link and frame so as to provide for heel height "presets." In yet other instances, the members may be configured so as to allow for a limited range of "free pivoting" of the ankle link. For example, a portion of the detent rod may be made smooth so as to not be capable of engaging the detent member. This will allow for free pivoting of the foot which would allow a user to insert the foot into a boot or other footwear. Once the free pivoting feature has been utilized, the user can activate the assembly so as to fixedly retain the detent rod over a then-adjustable range of motion.

In a relatively simple embodiment, as described with reference to FIG. 5, adjustability of the heel height is accomplished by depressing the button 39 directly connected to the detent assembly 32. In a number of instances, it is desirable for a user of the prosthetic foot to be able to adjust the heel height without directly accessing the foot itself. Various arrangements may be implemented to allow for such remote adjustment. For example, as shown in FIG. 6, fluid pressure may be utilized to activate the detent member. FIG. 6 shows a cross-sectional view of remotely activatable detent member 32 taken in a plane perpendicular to that of FIG. 5. As previously described, the detent includes a housing 37 having a slidable member 36 therein. The slidable member 36 is moved against a biasing force exerted by a spring 38 by depressing a button 39 so as to permit the detent rod (not shown) to be freed. In the FIG. 6 embodiment, a fluid delivery fitting 42 is disposed in the slidable member 36 so as to provide fluid communication to a fluid chamber defined between the slidable member 36 and inner portion of the button 39. The fluid delivery fitting 42 is in communication with a fluid line 44, and the assembly includes a set of O-rings 46, 46' which complete the fluid seal. In use, a fluid, typically air, is delivered to the detent member 32 from a source, typically a handheld bulb type pump. This air serves to displace the slidable member 36 thereby freeing the detent rod. In a typical application, it has been found that air having a pressure of approximately 15-20 pounds, and constituting a relatively small volume, may be reliably utilized to activate the detent assembly. Pressures of this type are readily achieved by a small handheld pump. In other embodiments, a fluid such as an oil may likewise be utilized to activate the system.

Yet other modes of activation may be readily implemented. For example, in some embodiments, a wire or cable may be utilized to provide a mechanical force for remotely activating the detent assembly. In yet other instances, activation may be electronic. For example, a solenoid or electromagnet may be utilized to provide for the release and retention of the detent rod. Other electronic activators such as linear actuators may be likewise employed. Also, while the fluid pump is described as being manually activated, it is to be understood that it could be powered by a battery or other such source.

In yet other instances, activation may be achieved through the use of shape memory alloy materials. As is known in the art, these alloys can be made to change their shape, and hence provide a mechanical force, in the course of doing so by the application of heat. Such heat can be applied through resistance heating. In one specific embodiment, a plurality of shape memory alloy wires, tubes or rods are disposed so as to extend along the length of the sliding member. One end of each body of shape memory material is anchored to the sliding member and a second end of each is coupled to the housing. The bodies of shape memory material are coupled to an electrical circuit so that a current may be selectably passed therethrough to heat the material. Alternatively, separate resistance heaters may be employed. Heating causes a change in the length of the bodies which in turn causes motion of the sliding member thereby actuating the detent. Still other modes of activation will be apparent to those of skill in the art.

Other embodiments of the device of the present invention may be readily implemented in accord with the teaching presented herein. For example, the detent assembly may be configured other than as is shown herein, and in that regard the detent rod and detent mechanism may include various mechanical features which could substitute for the grooves. Also, yet other detent mechanisms include locking wedges, screw retainers and the like may be incorporated. Also, the configuration and placement of the various mechanical features of the present invention may be varied as will be apparent to those of skill in the art. In view of the foregoing, it is to be understood that the drawings, discussion and description presented herein are illustrative of specific embodiments of the invention but are not meant to be limitations upon the practice thereof. It is the following claims, including all equivalents, which define the scope of the invention.

The invention claimed is:

1. A prosthetic foot having an adjustable height heel, said foot comprising:
    a frame portion;
    an ankle link which is pivotally supported by said frame portion at a first pivot axis;
    a detent rod which is pivotally connected to said ankle link at a second pivot axis; and
    a detent member pivotally affixed to said frame portion at a third pivot axis so that said detent rod passes through and extends between said second pivot axis and said third pivot axis, said detent member further includes a biasing mechanism and is selectively activatable to receive and releasably retain said detent rod so that the length of a portion of the detent rod extending between said second and third pivot axes may be selectively adjusted;
    whereby when said length is changed, the angular relationship of said frame portion and said ankle link is changed.

2. The prosthetic foot of claim 1, wherein said detent rod includes at least one groove formed thereupon and said detent member includes at least one corresponding groove which may be selectively engaged with at least a portion of said at least one groove of the detent rod.

3. The prosthetic foot of claim 1 wherein said detent rod includes an elongated length portion, and said detent member includes a housing having a slidable member disposed therein, said slidable member including a passage which is configured to allow a segment of said elongated length portion of said detent rod to pass therethrough, said biasing mechanism is selectively activatable to exert a biasing force on said slidable member so as to urge a portion of a wall of said passage into contact with a segment of said elongated length portion, whereby said detent rod is selectively retained thereby.

4. The prosthetic foot of claim 3, wherein said elongated length portion of said detent rod includes a groove formed thereupon, and said wall of said passageway which is urged into contact with the segment of the rod includes a groove which engages at least a portion of the groove on the elongated portion of the rod.

5. The prosthetic foot of claim 3, wherein said biasing mechanism includes a spring.

6. The prosthetic foot of claim 3, wherein said detent member has a fluid chamber therein which is in fluid communication with a fluid inlet, said fluid chamber being in mechanical communication with said slidable member so that the introduction of fluid into said chamber exerts a force on said slidable member so as to overcome said biasing force.

7. The prosthetic foot of claim 6, wherein said prosthetic foot further includes a pump operable to deliver a pressurized fluid to said fluid chamber.

8. The prosthetic foot of claim 1, wherein said detent member includes an actuator for activating said detent member to selectively release and retain said detent rod, said actuator being selected from the group consisting of: fluidic actuators, solenoids, linear actuators, shape memory actuators, mechanical actuators, and combinations thereof.

9. The prosthetic foot of claim 1, further including a resilient sole plate coupled to said frame portion.

10. The prosthetic foot of claim 9, wherein said foot further includes a cosmetic shell which is simulative of a human foot and which encloses and retains at least a part of the sole plate.

11. The prosthetic foot of claim 1, wherein said ankle link is configured to engage a prosthetic leg.

* * * * *